United States Patent [19]

Makovec et al.

[11] 4,317,795
[45] Mar. 2, 1982

[54] CATALYTIC ALKYLATION OF HYDROCARBONS

[75] Inventors: Donald J. Makovec; Donald M. Haskell, both of Bartlesville, Okla.

[73] Assignee: Phillips Petroleum Company, Bartlesville, Okla.

[21] Appl. No.: 124,994

[22] Filed: Feb. 26, 1980

Related U.S. Application Data

[62] Division of Ser. No. 27,425, Apr. 5, 1979, Pat. No. 4,207,423.

[51] Int. Cl.³ .......................... G01N 21/00; G05D 7/00
[52] U.S. Cl. ...................................... 422/62; 422/111; 422/115; 422/189; 422/235
[58] Field of Search .................. 422/62, 110, 111, 115, 422/189, 234, 235; 23/230 A; 585/701, 717, 332, 723, 724, 727, 730; 208/DIG. 1

[56] References Cited

U.S. PATENT DOCUMENTS

| | | | |
|---|---|---|---|
| 2,397,085 | 3/1946 | Boedeker et al. | 585/332 |
| 3,316,332 | 4/1967 | Glahn | 585/701 |
| 3,663,646 | 5/1972 | Chapman | 585/332 |
| 3,814,915 | 6/1974 | Sweeney, Jr. | 208/DIG. 1 |
| 3,953,538 | 4/1976 | Boney | 585/723 |
| 4,189,616 | 2/1980 | Liebert | 208/DIG. 1 |
| 4,205,196 | 5/1980 | Makovec | 422/111 |

Primary Examiner—William F. Smith
Assistant Examiner—Chris Konkol

[57] ABSTRACT

A continuous process for the alkylation of an alkylatable hydrocarbon with an alkylating agent in the presence of an acid-type catalyst, including; contacting an alkylatable hydrocarbon with an alkylating agent in the presence of an acid-type catalyst at a temperature and pressure and for a time sufficient to alkylate the alkylatable hydrocarbon; separating the reaction effluent stream into an alkylate product phase and a catalyst phase containing catalyst-soluble oil; cooling the catalyst phase to a temperature essentially equal to the alkylation reaction temperature; recycling the cooled catalyst phase to the alkylation reaction; contacting a diolefinic hydrocarbon with an acid-type catalyst at a temperature and pressure sufficient to form additional catalyst-soluble oil and combining the additional catalyst-soluble oil with the circulating catalyst phase. In accordance with another aspect of the invention, a quantity selected from the amount of catalyst-soluble oil, water and/or the total of the amount of catalyst-soluble oil and water in the catalyst phase is controlled, within specific limits. A start-up procedure and apparatus for carrying out the process are also included.

6 Claims, 3 Drawing Figures

CATALYTIC ALKYLATION OF HYDROCARBONS

This application is a divisional of copending application Ser. No. 027,425, filed Apr. 5, 1979, now U.S. Pat. No. 4,207,423 issued June 10, 1980.

BACKGROUND OF THE INVENTION

The present invention relates to a catalytic alkylation process and apparatus. In a more specific aspect, the present invention relates to a catalytic alkylation process in which an alkylatable hydrocarbon is contacted with an alkylating agent in the presence of an acid-type catalyst and the catalyst is cyclically circulated through the system. In yet another aspect, the present invention relates to a catalytic alkylation process and apparatus in which an acid-type catalyst is cyclically circulated through the system to produce an alkylate product of improved octane number.

Numerous processes are known in the prior art for alkylating an alkylatable hydrocarbon with an alkylating agent in the presence of a catalyst. From a commercial standpoint, the most prevalent systems involve the cyclic circulation of an acid-type catalyst, such as hydrofluoric acid, sulfuric acid, etc. through a reaction zone, a separation zone, a cooling zone and back to the reaction zone.

One such process for the alkylation of hydrocarbons, utilizing the cyclic circulation of the catalyst, introduces the reactant hydrocarbons in a gaseous phase. In this system the gaseous hydrocarbon feed mixture is introduced at a high velocity to the lower portion of the reaction zone and into a continuous catalyst phase maintained in the reaction zone. Suitable conditions of temperature and residence time are provided in the reaction zone whereby the alkylatable hydrocarbon is alkylated. A stream comprising catalyst, alkylate product and unconsumed reactants passes from the upper portion of the reaction zone into a settling zone, wherein separation occurs between the alkylate product phase and the catalyst phase. The alkylate product phase is withdrawn from the settling zone for further processing, as by fractionation, and the catalyst phase is passed downwardly to a cooling zone and thence back into the reaction zone.

Another process, based on the cyclic circulation of the catalyst, which overcomes certain of the inherent deficiencies of the gas phase process and permits operation at low reaction temperatures, introduces the reactant hydrocarbons in the liquid phase. In this process, the hydrocarbon reactants are introduced into the bottom of the reaction zone through constricted passageways, thereby creating a liquid lift system, whose motive power comes from the difference in density of the flowing streams and to some extent from the kinetic energy of the inlet hydrocarbon stream, and at the same time creating small droplets of reactants having a high interfacial area which result in a desirably high reaction rate. The reactant hydrocarbons and catalyst move upwardly through an elongated, tube-type reaction zone, the effluent, including alkylate product, catalyst and unreacted hydrocarbons, is discharged from the reaction zone into a settler-surge vessel, an alkylate product phase is withdrawn for further processing and a catalyst phase is passed downwardly through a tube-type conduit to a cooler and thence back into the reaction zone.

It has generally been recognized in the art that in order to obtain an alkylate product of maximum octane number, the weight percent total acidity of the catalyst should not exceed nor fall below certain quantities. While the tolerable acidity of the catalyst will vary depending upon the reactant hydrocarbons and the temperature of operation, it is generally thought that the total acidity of the catalyst under any conditions should not be higher than about 90 percent, that alkylate products of highest octane number are obtained at acidities substantially lower than this and, consequently, that the weight percent total acidity of the catalyst for optimum octane number should be between about 87 percent and 67 percent. Consequently, the catalyst is in some way diluted so as to maintain the desired total acidity. Obviously, water would be the logical diluting agent to utilize. However, the presence of excessive amounts of water, in systems utilizing acid catalysts, creates problems in that, in conjunction with the acid, water is highly corrosive to the alkylation system and catalyst handling system. Therefore, the acid catalyst is normally utilized in an essentially anhydrous condition. There is a tendency in alkylation systems for water to accumulate as the result of its presence in the hydrocarbon reactants and its absorption from the atmosphere. Therefore, alkylation systems employing acid-type catalysts normally include a so-called catalyst "rerun" system through which catalyst is at least periodically passed in order to remove water therefrom. The rerun system will normally involve withdrawing a portion of the catalyst phase as it flows from the separator to the cooler. The withdrawn catalyst phase is heated to a temperature sufficient to vaporize residual alkylate, unreacted hydrocarbons, and the major part of the acid phase from the water. Water is withdrawn as a bottoms product from the rerun separator while the vapor phase is recycled to the settler-surge zone or back to the separated acid phase. Generally, a portion of the alkylatable hydrocarbon, in liquid form, is utilized as a reflux and another portion, in gaseous form, as a stripping medium in the rerun separator.

It is also recognized in the art that a certain amount of dilution of the catalyst phase occurs in the reaction zone itself. Specifically, what is known as a catalyst- or acid-soluble oil (ASO) is produced in the reaction zone, which inherently acts as a diluent for the catalyst phase. While the specific nature of the acid-soluble oil has not been completely established, it is generally accepted that it comprises predominantly polymeric materials with minor amounts of complexes and small or trace amounts of impurities, such as sulfur, to the extent such impurities exist in the alkylation feed materials. These catalyst-soluble oils are retained in the catalyst phase during the separation of the alkylate phase from the catalyst phase and consequently are recycled to the alkylation system. It has also been universally accepted, by those skilled in the art, that the production of catalyst-soluble oil is substantially in excess of that necessary or desirable for dilution of the catalyst. Consequently, the prior art contains suggestions for the removal of the excess catalyst-soluble oil.

Finally, those skilled in the art have recognized the fact that under normal operating conditions the production of catalyst-soluble oils is extremely slow. Accordingly, the prior art has suggested various start-up procedures which will rapidly produce the desirable inventory of catalyst-soluble oil, thereby substantially shortening the time necessary to arrive at full-scale production of alkylate product.

SUMMARY OF THE INVENTION

A continuous process for the alkylation of an alkylatable hydrocarbon with an alkylating agent in the presence of an acid-type catalyst, including; contacting an alkylatable hydrocarbon with an alkylating agent in the presence of an acid-type catalyst at a temperature and pressure and for a time sufficient to alkylate the alkylatable hydrocarbon; separating the reaction effluent stream into an alkylate product phase and a catalyst phase containing catalyst-soluble oil; cooling the catalyst phase to a temperature essentially equal to the alkylation reaction temperature; recycling the cooled catalyst phase to the alkylation reaction; contacting a diolefinic hydrocarbon with an acid-type catalyst at a temperature and pressure sufficient to form additional catalyst-soluble oil and combining the additional catalyst soluble oil with the circulating catalyst phase. In accordance with another aspect of the invention, a quantity selected from the amount of catalyst-soluble oil, water and/or the total of the amount of catalyst soluble oil and water in the catalyst phase is controlled, within specific limits. A start-up procedure and apparatus for carrying out the process are also included.

Inasmuch as there is some confusion of terminology in the art as to which of the reactants is the alkylatable hydrocarbon and which is the alkylating agent, the isoparaffin hydrocarbon, when referred to herein, will be referred to as the "alkylatable hydrocarbon" while the olefinic hydrocarbon will be referred to herein as the "alkylating agent".

DETAILED DESCRIPTION OF THE INVENTION

Figure 1:
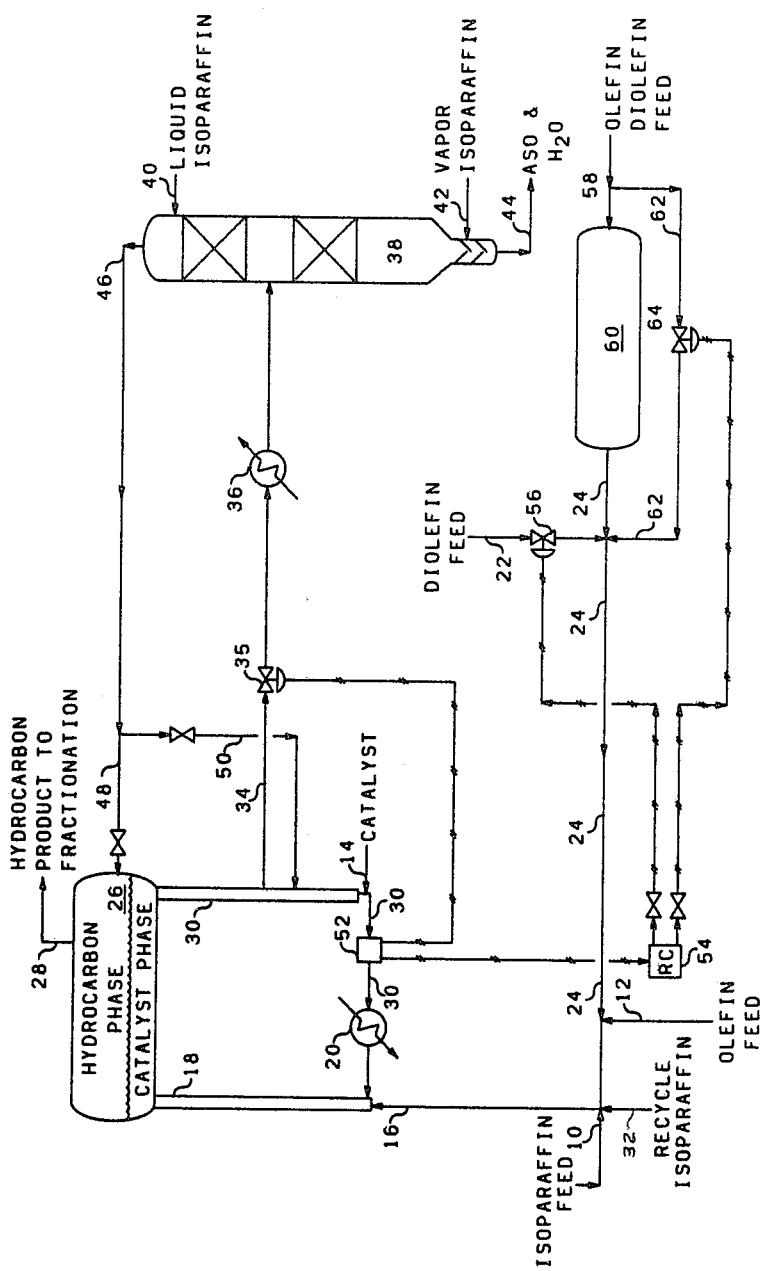
FIG. 1 is a simplified flow diagram of an alkylation system in accordance with one embodiment of the present invention.

While, as previously indicated, the present invention can be carried out in any type of reactor system utilizing a cyclically flowing, acid-type catalyst, the preferred system in accordance with the present invention is a cyclic catalyst system in which the mixture of hydrocarbon feed materials is maintained in a liquid state. Such a system is described in detail in U.S. Pat. No. 3,213,157, which is incorporated herein by reference. Briefly, the system comprises a vertically-disposed tubular reactor into which a mixture of the hydrocarbon feed materials and the catalyst is introduced adjacent to the bottom of the reactor, a horizontally-disposed settler-surge vessel, adapted to receive effluent from the top of the reactor and separate the effluent into an alkylate product phase, which is further processed by fractionation or the like, and a catalyst phase, a vertically-disposed tubular catalyst return conduit wherein the catalyst phase passes downwardly, and an essentially horizontally-disposed acid phase cooler, which is cooled by water. This entire system is in open communication throughout for cyclic catalyst flow. Normally, acid phase is at least periodically withdrawn as a side stream from the separated acid phase conduit and passed to a heater where it is heated to a temperature sufficient to cause separation of a liquid phase, comprising predominantly water and some acid-soluble material, and a vapor phase comprising predominantly catalyst, unreacted feed materials and some alkylate. The heated acid phase is then passed to a rerun separator, which is normally operated with a liquid portion of the alkylatable hydrocarbon, as a reflux, and a vapor portion, as a stripping agent. The vapor phase product of the rerun separator is then returned to the system's settler-surge vessel or back to the catalyst phase at a point below or downstream from the point at which catalyst phase was withdrawn for rerun, while the water and any acid-soluble material present is withdrawn as a liquid phase and discarded.

A variety of alkylation catalysts can be employed in the alkylation reaction, including well known acid catalysts such as sulfuric acid, hydrofluoric acid, phosphoric acid; metal halides, such as aluminum chloride, aluminum bromide, etc.; and other alkylation catalysts. A preferred catalyst for use in the present invention is hydrofluoric acid.

The reaction may be carried out at pressures varying from atmospheric to as high as 1000 psi and higher, preferably about 125 to 225 psia, and at space velocities from about 0.1 to about 20. The pressure is preferably sufficient to maintain the hydrocarbon reactants in their liquid phase.

In an alkylation reaction, involving the alkylation of isoparaffins with olefins, a substantial molar excess of isoparaffin to olefin is employed to provide a feed ratio in excess of 1/1, usually about 4/1 to about 70/1 and preferably about 5/1 to about 20/1.

As previously indicated, the reaction zone is preferably maintained under sufficient pressure to insure that the hydrocarbon reactants and the alkylation catalyst are in a liquid phase. The temperature of the reaction will vary with the reactants and with the catalyst employed but generally ranges from between about $-40°$ F. to about 150° F. However, in the reaction of an isoparaffin, such as isobutane, with a $C_4$ olefin, such as butylenes, butene-1 and/or butene-2's, the reaction temperature is preferably between about 60° and about 100° F. and, ideally, about 70° to about 90° F.

Conventionally, the alkylation reaction can comprise reaction of an alkylatable isoparaffin with an olefin or other alkylating agent, the reaction of a nornal paraffin with an olefin or other alkylating agent or the reaction of an aromatic hydrocarbon with an olefin or other alkylating agent. In one embodiment of the present invention, the reaction involves the alkylation of an an isoparaffin with an olefin. More specifically, the isoparaffin may be isopentane or isobutane, preferably the latter, while the olefin may be propylene, a butene or mixture of butenes, such as isobutylene, butene-1 and/or butenes-2, amylenes, hexenes and mixtures thereof. A particularly useful olefin mixture is a product of a catalytic cracking operation. Normally, such a product will contain propane, propylene, isobutane, n-butane, isobutylene, butene-1, trans- and cis-butene-2, butadiene and small amounts of $C_5$ plus hydrocarbons. This mixture can be fractionated to remove propane and propylene and $C_5$ and higher hydrocarbons, thus leaving a "butenes" mixture of normal butane, isobutane, butene-1, isobutylene and butene-2's. However, it has been found that in the reaction of an isoparaffin, particularly isobutane, with a $C_4$ olefin, such as isobutylene, butene- 1 and/or butene-2's, acid-soluble oil is difficultly formed and is formed in extremely small amounts, thus resulting in a net loss of acid-soluble oil during the operation of the alkylation reaction. When such butene mixtures are the preferred feed material, improved results are obtained by hydroisomerizating the feed in order to convert butene-1 to butene-2's. Following hydroisomerization, the feed will be made up of a predominant amount of butene-2's, lesser amounts of isobutylene and still smaller amounts of butene-1, and optionally isobutane. In the latter instance, the mixture will generally contain a major proportion of isobutane and small amounts of normal butane. In any event, such hydroisomerization reduces the butadiene content to trace amounts. However, in accordance with the present invention, it has been found that butadiene forms catalyst-soluble oil, suitable for catalyst dilution, at a rapid rate and in subtantially greater volumes than are formed by the monoolefin feed materials normally employed, particularly a butenes feed. Consequently, in accordance with one aspect of the present invention, butadiene is at least periodically added to the reaction system in controlled amounts in order to maintain a predetermined concentration of catalyst soluble oil in the system. Such addition may be to the feed materials or to the recycled catalyst phase. Since the temperature of the recycle catalyst upstream of the catalyst cooler is above the temperature of the reaction zone, the quantity of and the speed with which catalyst-soluble oil is formed is further improved by addition to the catalyst phase. Further improvement may be attained by heating the added butadiene to a temperature above the reaction temperature, and preferably above the temperature of the recycle catalyst, prior to its addition to the circulating catalyst. It is also possible to form the catalyst-soluble oil outside the reaction system, per se, prior to addition thereof to the circulating catalyst phase. In this case, the butadiene is reacted with a portion of the recycle catalyst phase, or preferably with fresh or rerun catalyst, in a separate stirred reactor and at a controlled temperature and pressure most conducive to the formation of catalyst soluble oil. Where a butene-rich catalytic cracking effluent stream is utilized as an alkylation feed and such effluent is hydroisomerized, the added butadiene may be obtained by at least periodically by-passing a portion of the catalytic cracking effluent around the hydroisomerization reaction. Obviously, this by-pass stream may be added in any of the manners previously described.

It has also been found that, if the amount of catalyst-soluble oil in the catalyst phase drops below about 0.4 weight percent of the total catalyst phase, the octane number of the resultant alkylate drops considerably, in fact, as much as about 2.5 to 3 octane numbers. On the other hand, if the amount of catalyst-soluble oil is above about 8 weight percent, complications are introduced by the formation of an emulsion between the catalyst-soluble oil and the water present in the system. Consequently, the catalyst soluble oil content of the catalyst phase should be between about 0.4 and 8 weight percent, and preferably between about 0.5 and about 6 percent. It has further been found that the catalyst-soluble oil may be substituted for a significant part of the water normally present in the system as a catalyst phase diluent, thereby reducing corrosion of the system which results from the presence of water. Accordingly, it has been found that the water content of the catalyst phase should be between about 0.5 and 5.0 weight percent, preferably below about 2 weight percent of the total catalyst phase and still more preferably below about 1.5 weight percent. The sum of the amount of catalyst-soluble oil and water in the catalyst phase should be between about 0.9 and about 25 weight percent of the total catalyst phase, preferably between about 0.9 and about 12 weight percent and still more preferably between about 3 and about 6 weight percent. The total acidity of the catalyst phase is desirably between about 70 and 95 weight percent and preferably between about 85 and about 90 weight percent. The difference between the total acidity of the catalyst phase and the total amount of catalyst-soluble oil and water in the catalyst phase is reflected in the fact that a small amount of the alkylatable hydrocarbon is also soluble in the catalyst phase and will be contained therein and recycled to the reactor with the catalyst phase.

In light of the above, yet another aspect of the present invention, involves control of the amount of catalyst-soluble oil and water in the circulating catalyst phase, preferably within the critical limits set forth above. Specifically, the amounts of catalyst-soluble oil, water and/or the total amount of these components, in the circulating catalyst phase are at least periodically determined; and the amount thereof is at least periodically adjusted to maintain predetermined amounts in the circulating catalyst phase. Excessive amounts of water, catalyst-soluble oil or total water and catalyst soluble oil are removed by at least periodically adjusting the passage of circulating catalyst phase to the catalyst rerun system and deficiencies in the amount of catalyst-soluble oil are adjusted by at least periodically contacting a mono- or diolefin hydrocarbon with acid-type alkylation catalyst to produce catalyst soluble oil and combining the catalyst soluble oil thus generated with the circulating catalyst phase, as previously described. Suitable olefinic hydrocarbons include any of the alkylating agents normally utilized, such as propylene and butenes and mixtures thereof, $C_5$ and higher monoolefins, and mixtures thereof, a portion of the monoolefinic alkylation feed material and/or a diolefinic hydrocarbon. A preferred olefinic material is butadiene and mixtures thereof with monoolefins or other diolefins.

When catalyst-soluble oil is generated outside the alkylation reaction system, suitable operating conditions include, a ratio of catalyst to olefin between about 0.5 and 5.0, a temperature between about 50° and about 150° F., a pressure between about 50 and about 200 psia (liquid phase) and a reaction time between about 5 and about 60 minutes for a batch operation or its equivalent.

In addition to maintaining a controlled quantity of catalyst soluble oil in the recirculating catalyst, it has also been found, in accordance with another embodiment of the present invention, that the time required to start-up an alkylation reaction can be greatly reduced by building up the desired inventory of catalyst-soluble oil in the circulating catalyst by the rapid and efficient formation of catalyst-soluble oil from butadiene, as previously described. Specifically, at the outset of a start-up procedure butadiene is continuously added to the circulating catalyst, in one of the previously described manners, until the desired inventory of catalyst-soluble oil is present in the circulating catalyst and thereafter at least periodically to maintain the desired amount of catalyst-soluble oil.

In a conventional start-up procedure for an alkylation reaction system, the alkylatable hydrocarbon is circulated through the alkylation reactor, the settler-surge vessel, and an alkylate phase fractionator, in which alkylatable hydrocarbon is removed for recycle to the reactor, while reaction conditions of temperature, pressure, etc., are maintained. Once the optimum alkylatable hydrocarbon flow is established, catalyst is introduced and circulated through the reactor, settler-surge vessel, the catalyst cooling unit and back to the reactor to establish the preferred catalyst flow rate. Finally, the alkylating agent is introduced as a mixture with the alkylatable hydrocarbon, or separately, into the reaction zone until its preferred flow rate is established. In the practice of the present invention, the diolefin, utilized herein to generate acid-soluble oil, may be introduced at varying points in time during the start-up cycle. In this instance, the catalyst may first be cycled through the system and the diolefin added directly thereto or the diolefin may be introduced through one or both of the alkylating agent or alkylatable hydrocarbon feed lines or directly into the reactor. It is also possible to introduce the alkylating agent and catalyst and then add the diolefin or introduce both the alkylating agent and alkyatable hydrocarbon as well as the catalyst prior to the introduction of the diolefin. In any event, during the start-up procedure the diolefin is contacted with the catalyst under alkylation reaction conditions or at conditions more conducive to catalyst-soluble oil formation. Where a butenes mixture is utilized as the olefin feed, the diolefin may be mixed with the olefin feed or the circulating catalyst. Normally, the mixture will pass through a hydroisomerization system and the diolefin will be hydrogenated and, therefore, not appear in the feed to the alkylation reaction vessel. However, the olefin-diolefin mixture will, during startup, be bypassed around the hydroisomerization system so that the inventory of catalyst-soluble oil in the catalyst phase may be built up. Once the predetermined level of catalyst-soluble oil in the catalyst phase has been built up to the predetermined desired level, this level may be maintained by at least periodically introducing additional diolefin to the reaction system depending upon the catalyst soluble oil.

The invention will be further illustrated by reference to the drawings.

In accordance FIG. 1 of the drawings, which refers to a specific set of conditions and feed materials of one embodiment, the isoparaffinic feed is introduced through line 10, olefinic feed through line 12 and catalyst through line 14. Usually during startup of the system, isoparaffin alone is first passed through 10 and line 16 to the bottom of tube-type reactor 18. After the flow rate of the isoparaffin has been established, acid will be introduced through line 14 and water-cooled cooler 20 to reactor 18. In actual practice, however, the cooler 20 is generally a horizontally-disposed, elongated cooler and line 16 introduces feed materials to one end of cooler 20 adjacent the bottom of reactor 18 while catalyst is introduced in the cooler 20 upstream of the point of introduction of feed materials through the cooler 20. During the start-up procedure, whether catalyst is first introduced or is introduced after introduction of isoparaffin feed, diolefin is introduced through line 22 and line 24, where it either mixes with isoparaffin feed through line 16 or is introduced directly into the reactor 18 or cooler 20. Once the desired inventory of acid-soluble oil is built up in the catalyst phase, the olefin feed will then be introduced usually as a mixture with the isoparaffin feed and in most cases in admixture with diolefin feed. Consequently, in the usual operation, diolefin feed, olefin feed and isoparaffin feed are combined and introduced through line 16.

A reactor effluent stream from reactor 18 is passed to settler-surge vessel 26. In settler-surge vessel 26 the effluent is separated into an alkylate phase, which is discharged through line 28, and a catalyst phase, which is discharged through conduit 30. From conduit 30 the catalyst phase passes through the cooler 20 and back to reactor 18. The alkylate phase passing through line 28 passes through a fractionation system (not shown) where isoparaffin is recovered and is then recycled to the reaction system through line 32. Once the desired flow rates of acid and reactants have been established and the desired inventory of acid-soluble oil has been built up, the reaction will proceed in a normal manner and the diolefin feed will be discontinued. However, it is desirable that the diolefin feed be at least intermittently introduced in order to maintain the desired level of acid-soluble oil in the catalyst phase. During operation of the alkylation reaction and particularly in the embodiment in which water is to be maintained below a specified level the catalyst phase passing through line 30 is continuously or intermittently withdrawn through line 34, passes through control valve 35 and a heater 36 and thence to rerun system 38. Rerun system 38 is supplied with a liquid isoparaffin, as the reflux medium, through line 40 and a vapor phase isoparaffin, as a stripping medium, through line 42. A vapor phase including isoparaffin, catalyst and residual amounts of alkylate is discharged through line 46 and recycled to the system through lines 48 or 50. Rerun system 38 may also comprise a series of appropriately heated and pressure-controlled flash units adapted to separate water, purified catalyst, which may be reintroduced as rerun catalyst through line 14 as needed, unreacted recycle isoparaffin, which may be combined with isoparaffin feed through line 32 and small amounts of alkylate may be returned to separator-surge vessel 26 through line 48 or added to the alkylate phase. The heated catalyst phase is separated in rerun system 38 to produce a bottoms fraction comprising water and acid-soluble oil, which is discharged through line 44, and a vapor phase comprising catalyst, isoparaffin and small amounts of alkylate product, which are discharged through line 46. The vapor phase from rerun unit 38 may be recycled back to settler-surge vessel 26 through line 48 or back to catalyst phase conduit 30 through line 50.

In order to maintain a proper amount of diolefin feed in the acid phase, both during startup and operation of the alkylation reaction, it is preferred that the amount of acid-soluble oil in the catalyst phase be at least periodically determined. For this purpose, a detector system 52 determines the amount of acid-soluble oil in the catalyst phase, transmits a signal to controller 54 and controller 54 in turn sends a signal to valve 56 which controls the volume of diolefin feed introduced in accordance with the measured amount of acid-soluble oil in the catalyst phase.

In that embodiment of the present invention in which the olefin feed is a butenes mixture, as from a catalytic cracker, the olefin feed is preferably introduced through line 58 to hydroisomerization unit 60. In hydroisomerization unit 60, butene-1 is converted to butene-2's, which are then discharged through line 24 where they mix with isoparaffin feed and are then passed through line 16 to reactor 18. In this particular embodiment, the catalytic cracker effluent will usually contain sufficient diolefin to generate catalyst soluble oil, but if it does not or a butenes stream devoid of butadiene is used, it is convenient to add diolefin to the feed through line 22. Normally, during startup, the mixture of olefin-diolefin will be bypassed around hydroisomerization unit 60 through line 62 and control valve 64. When sufficient acid soluble oil is present in the catalyst phase, all of the olefin-diolefin mixture will be passed through hydroisomerization unit 60 so that all the olefin feed is discharged through line 24. During normal operation of the reaction, diolefin may then be bypassed around hydroisomerization unit 60 through line 62 as needed, under control of valve 64, or it may be introduced through line 22 from an outside source or both in order to maintain the desired level of acid-soluble oil in the catalyst phase. For purposes of controlling the amount of diolefin being fed to the reactor system valve 64 in line 62 and/or valve 56 in line 22 may be appropriately connected to controller 54.

In that embodiment of the invention in which the amount of water and/or the total amount of water and catalyst soluble oil in the recycle catalyst phase is to be controlled, the amount of water and/or water plus catalyst soluble oil is detected by detector system 52 and an appropriate signal will be transmitted to control valve 35. Control valve 35 will control the volume and/or timing of the passage of catalyst phase to rerun system 38. Since, in this embodiment, more water is removed than is conventionally done, more catalyst-soluble oil will generally also be removed from the catalyst phase. Consequently, it will be necessary to at least periodically add catalyst soluble oil to the catalyst phase, even though in some modes of operation, as in some cases when the olefin feed is propylene or $C_5$ or higher mono-olefins, there would normally be a net excess of catalyst-soluble oil present.

Figure 2:
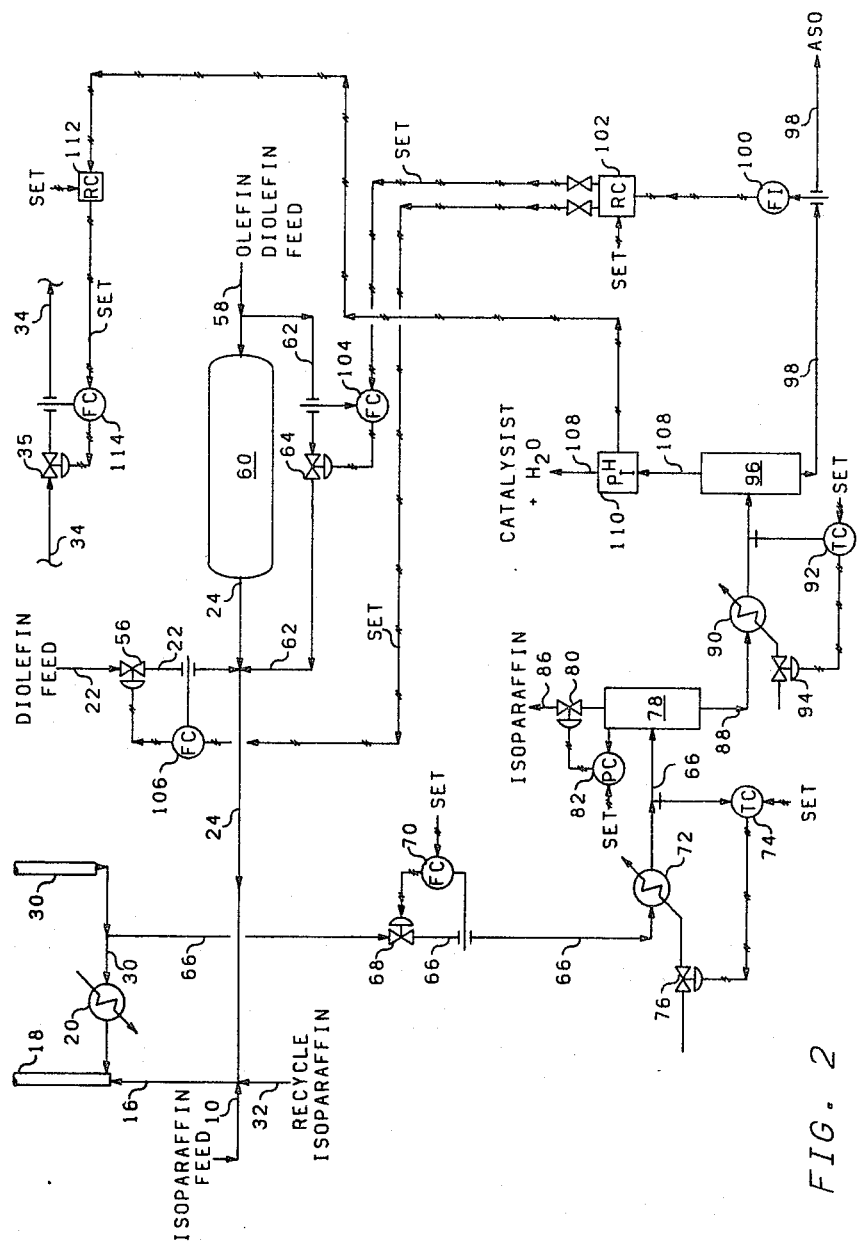
FIG. 2 is a more detailed diagram of a control means for the system of FIG. 1.

FIG. 2 illustrates an appropriate control system. A sample of catalyst phase passes through line 66, valve 68 controlled by flow controller 70 and temperature adjusting means 72. Temperature adjusting means 72 will be either a heater or a cooler, depending upon the alkylation reaction temperature and ultimately the temperature of the catalyst phase. In any event, the temperature is controlled by temperature controller 74 which, in turn, controls valve 76 in the heating or cooling medium line to temperature adjusting means 72. The temperature is adjusted so as to flash off substantially only isoparaffin when the catalyst phase is passed to flash-separator means 78. Flash-separator 78 is maintained under a reduced pressure, for example about 22 psi, by control valve 80 and pressure controller 82. Flash-separator means 78 may be provided with a bottom reboiler and a reflux system, as will be apparent to one skilled in the art. The vaporized isoparaffin is discharged through line 86 to be disposed of or added to the isoparaffin feed as appropriate. The remainder of the catalyst phase is discharged as a bottoms through line 88 and heater 90. Heater 90 is controlled by temperature controller 92 and valve 94 in the heating medium line to heater 90. This controlled temperature will be, for example, about 250° F. The heated remaining catalyst phase is fed to flash-separator 96 which is operated to separate catalyst and water as a vapor phase and catalyst-soluble oil as a bottoms product. Flash-separator 96 may be bottom heated or reboiled and pressure-controlled or pressurized, as will be obvious to one skilled in the art. Catalyst-soluble oil is discharged through line 98 for disposal of reuse. The amount of catalyst-soluble oil flowing through line 98 is measured by flow indicator 100 which transmits a signal to recorder-controller 102 which, in turn, sends an appropriate signal to flow controller 104, connected to control valve 64, and/or flow controller 106, connected to control valve 56, as desired. Vaporized catalyst and water are discharged through line 108 for disposal or recovery of the catalyst. In order to simplify the operation, the catalyst and water are compressed or cooled to liquefy the same and the pH is measured by an automatic indicator or detector 110, such as an amperometric, conductometric or coulometric system. The measured pH signal is transmitted to recorder controller 112 where it is converted to percent or volume of water and an appropriate signal is sent to flow controller 114, which is connected to control valve 35 in catalyst rerun flow line 34. If the total of water and catalyst soluble oil is to be controlled pH indicator 110 would be substituted for by a flow indicator or recorder controller which would send an appropriate signal to recorder controller 112 which, in turn, would operate on this signal and a pH signal from indicator 110 to produce an output signal representative of the total of the water and catalyst-soluble oil.

Figure 3:
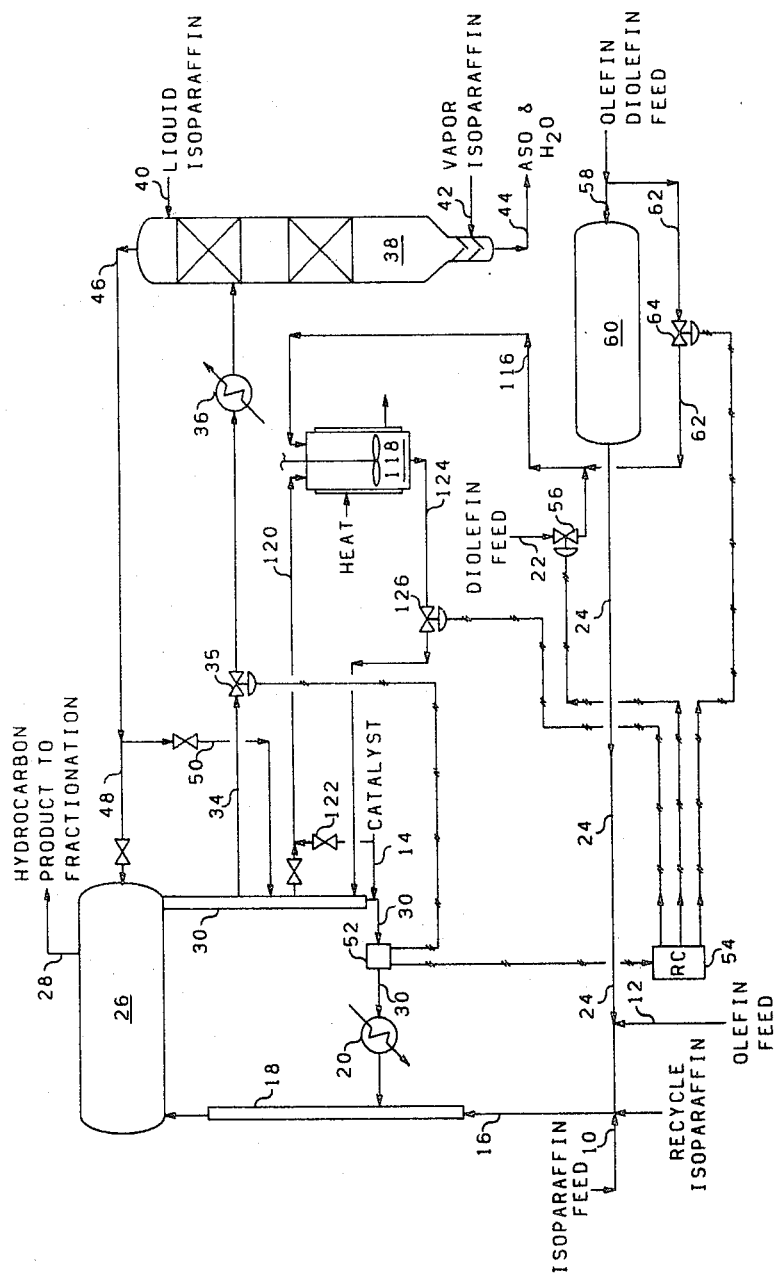
FIG. 3 is a simplified flow diagram of a second embodiment of the present invention.

In the embodiment of FIG. 3, the diolefin utilized to generate catalyst-soluble oil is heated or heated and contacted with catalyst, outside the alkylation system proper, and then combined with the circulating acid phase. In the variation shown, diolefin is passed through line 116 to reactor 118. Reactor 118 is preferably stirred and heated to a temperature appropriate for the formation of catalyst soluble oil, preferably above the alkylation reaction temperature and still more desirably above the temperature of the circulating catalyst phase. Catalyst is supplied to reactor 118, as a portion of the catalyst phase through line 120, or preferably, as fresh or rerun catalyst from line 14 through line 122. Catalyst-soluble oil from reactor 118 is combined with the circulating catalyst phase through line 124. In this case, it may be most convenient to control the addition of catalyst-soluble oil by sending an appropriate signal from recorder controller 54 to control valve 126 in line 124. While not specifically shown, reactor 118 may be substituted for by a simple heater adapted to heat diolefin from line 116 to a temperature above the temperature of the circulating catalyst phase and add the heated diolefin to the circulating catalyst phase through line 124.

The control system may be electrical, mechanical, pneumatic or any combination of such conventional control systems.

The following examples will illustrate the operation of certain preferred embodiments of the present invention.

EXAMPLE I

In a series of continuous pilot plant tests, a butenes feed from a catalytic cracking operation was utilized as the alkylating agent feed, together with butadiene for producing catalyst-soluble oil and isobutane as the alkylatable hydrocarbon feed. The composition of the feed materials and analysis of the catalyst phase, the reaction conditions and an analysis of the alkylate product are set forth in the following Table I for a typical run with butadiene added to the butenes feed.

TABLE I

|  | Run 1 |
|---|---|
| Butenes Feed, cc/hr., | 2124 (20.41 vol % olefin plus diolefin) |

TABLE I-continued

| Composition | Vol. % |
|---|---|
| Propane | 0.24 |
| Butenes-2 | 12.52 |
| Butene-1 | 1.29 |
| Isobutylene | 6.03 |
| Normal butane | 2.84 |
| Isobutane | 76.51 |
| Butadiene | 0.57 |

| Isobutane, cc/hr. (Feed plus Recycle), | 3,876 |
|---|---|
| Composition | Vol. % |
| Isobutane | 98.5 |
| Normal Butane | 0.9 |
| Propane | 0.6 |

| Catalyst, cc/hr. | 34,980 (9.2 gal/hr) |
|---|---|
| Composition | Wt. % |
| HF | 85.8 |
| $H_2O$ | 2.2 |
| Hydrocarbon (Light) | 8(a) |
| Polymer Oil | 4.0 |
| Reactor: | |
| Pressure, (to maintain liquid) | 150 psig |
| Temperature, °F. | 90 |
| HF to Total Hydrocarbon vol. ratio, | 5.8 |
| Total Isobutane/Olefin + Diolefin mol ratio, | 11.2 |
| Alkylate (debutanized) cc/hr., | 770 |
| RON clear | 96.9 (estimated)(b) |

(a) dissolved isobutane
(b) calculated by components in alkylate

When butadiene was not charged to the system, the amount of acid-soluble oil present in the catalyst phase dropped to about 0.4 weight perecent. Under these conditions, the research octane number (clear) also dropped to 95.3. In this particular instance, the same rates of flow and operating conditions were utilized as in the runs in which butadiene was added to the system.

In the hydroisomerization unit a catalyst such as palladium on alumina in an amount of 0.05 weight percent can be utilized, at a pressure of about 120 to 130 psig, preferably 125 psig, a temperature at the inlet of about 200° F. and at the outlet of about 270° F., a weight hourly space velocity, pound per pound per hour, of about 150 to about 200 and preferably about 180 and a hydrogen-to-feed mol ratio of about 1/100 to 10/100. The upper limits will generally apply when the feed contains larger amounts of diolefins and sulfur.

EXAMPLE II

Another series of tests was conducted in order to determine whether the acid-soluble oil generated by the introduction of diolefin could be substituted for at least a part of the water normally present in the catalyst phase. In this case, a mixed butenes feed having about 25 percent by volume of butene-1, about 30 percent by weight of isobutylene and about 45 percent by weight of butene-2's was utilized. Table II, below, lists the conditions of operation, the analysis of the catalyst phase and the alkylate properties for four runs utilizing varying amounts of catalyst soluble oil as a diluent for the catalyst replacing varying amounts of water.

TABLE II

| | Run 2 | Run 3 | Run 4 | Run 5 |
|---|---|---|---|---|
| Alkylation Conditions: | | | | |
| IC4/olefin vol. feed, ratio, | 12.9 | 13.1 | 7.2 | 7.2 |
| Reactor temp., °F. | 90 | 90 | 70 | 70 |
| Nozzle Press. Drop, psi, | 35 | 34.5 | 36 | 32 |
| Acid Data, Wt. %: | | | | |
| $H_2O$ | 3.0 | 1.4 | 2.2 | 1.7 |
| HF | 92.5 | 90.1 | 89.1 | 89.2 |
| ASO | 0.7 | 2.9 | 3.4 | 3.6 |
| (ASO + $H_2O$) | (3.7) | (4.3) | (5.6) | (5.3) |
| Alkylate Properties(c): | | | | |
| Estimated RON + 0 ⎞ Butane- | 95.3 | 95.6 | 95.0 | 94.8 |
| Estimated RON + 3 ⎠ free | 108.8 | 110.0 | 108.7 | 108.6 |
| Eng. Determined RON + 0 | 96.1 | 96.7 | 96.3 | 96.4 |
| Eng. Determined RON + 3 | 107.0 | 107.1 | 107.7 | 108.0 |

(c) Calculated from components in alkylate

While specific materials, amounts thereof and operating procedures have been referred to herein, numerous variations and modifications thereof will be apparent to one skilled in the art and the present invention is considered to include such variations and modifications.

We claim:

1. Apparatus for producing a hydrocarbon alkylate product, comprising;
   alkylation reactor means adapted to alkylate an alkylatable hydrocarbon with an alkylating agent in the presence of an acid-type catalyst;
   separator-surge vessel means adapted to receive alkylation reactor effluent from said alkylation reactor and separate said effluent into an alkylate product phase and a recycled catalyst phase;
   first conduit means for recycling said separated catalyst phase to said alkylation reactor;
   cooling means in said first conduit means;
   hydroisomerization reactor means;
   second conduit means adapted to introduce an alkylating agent to said hydroisomerization means;
   third conduit means adapted to receive effluent product from said hydroisomerization reactor and introduce said effluent to said alkylation reactor; and
   bypass conduit means adapted to at least periodicially bypass at least a portion of the alkylating agent around said hydroisomerization reactor and directly to said alkylation reactor.

2. Apparatus in accordance with claim 1 wherein the bypass conduit means includes a control valve means adapted to control the amount of the alkylating agent passing through said bypass conduit means directly to the alkylation reactor.

3. Apparatus in accordance with claim 1 wherein the apparatus includes detector means operatively connected to the first conduit means and adapted to at least periodically determine the amount of catalyst soluble oil in the recycled catalyst phase and control means operatively connected to the bypass conduit means for adjusting the amount of alkylating agent bypassed around the hydroisomerization reactor.

4. Apparatus in accordance with claim 1 wherein the alkylation reactor is adapted to contact the alkylatable hydrocarbon with the alkylating agent in the presence of the catalyst in a liquid phase.

5. Apparatus in accordance with claim 3 wherein the detector means includes means for sampling the recycled catalyst phase, separating means adapted to separate catalyst-soluble oil from the sample of recycled catalyst phase and measuring means for measuring the amount of separated catalyst-soluble oil.

6. Apparatus in accordance with claim 3 wherein the control means is a flow control means.

* * * * *